(12) United States Patent
Press (10) Patent No.: US 10,709,602 B2
(45) Date of Patent: Jul. 14, 2020

(54) DEVICE FOR THE APPLICATION OF ELECTRICAL STIMULATION IN COMBINATION WITH MANUAL THERAPY

(71) Applicant: Robert M. Press, Wyckoff, NJ (US)

(72) Inventor: Robert M. Press, Wyckoff, NJ (US)

( * ) Notice: Subject to any disclaimer, the term of this patent is extended or adjusted under 35 U.S.C. 154(b) by 189 days.

(21) Appl. No.: 15/995,216

(22) Filed: Jun. 1, 2018

(65) Prior Publication Data

US 2018/0360648 A1    Dec. 20, 2018

Related U.S. Application Data

(60) Provisional application No. 62/520,704, filed on Jun. 16, 2017.

(51) Int. Cl.
*A61F 7/00* (2006.01)
*A61F 7/02* (2006.01)
*A61N 1/36* (2006.01)
*A61N 1/04* (2006.01)

(52) U.S. Cl.
CPC ............... *A61F 7/007* (2013.01); *A61F 7/02* (2013.01); *A61N 1/36021* (2013.01); *A61F 2007/0052* (2013.01); *A61F 2007/0087* (2013.01); *A61F 2007/0096* (2013.01); *A61F 2007/0295* (2013.01); *A61M 2205/054* (2013.01); *A61N 1/0452* (2013.01)

(58) Field of Classification Search
None
See application file for complete search history.

(56) References Cited

U.S. PATENT DOCUMENTS

| | | | |
|---|---|---|---|
| 5,097,828 A | 3/1992 | Deutsch | |
| 5,336,255 A | 8/1994 | Kanare | |
| 5,458,119 A * | 10/1995 | Vanharanta | A61B 5/0051 600/557 |
| 6,021,348 A | 2/2000 | James | |
| 6,567,696 B2 | 5/2003 | Voznesensky | |
| 8,641,648 B2 * | 2/2014 | Colloca | A61H 1/008 601/101 |
| 9,082,272 B2 | 7/2015 | Mohn | |
| 9,084,665 B2 * | 7/2015 | Beardall | A61N 1/32 |
| 2003/0216728 A1 | 11/2003 | Stern | |
| 2010/0228304 A1 | 9/2010 | Kriksunov | |
| 2011/0239701 A1 | 9/2011 | Simon | |
| 2017/0028196 A1 | 2/2017 | Stopperan | |

* cited by examiner

*Primary Examiner* — Brian T Gedeon
(74) *Attorney, Agent, or Firm* — Richard Malagiere, Esq.

(57) ABSTRACT

A device and method for the treatment of a patient by means of manual therapy through a hand held device along with simultaneous thermal treatment and electrical stimulation. The device is comprised of a handle with a finger grip, a shaft with removable applicator tips that can be heated or cooled as necessary. An electrical connection on the device handle allows for the incorporation of commercially available transcutaneous electrical stimulation units with the device to provide electrical stimulation in combination with manual and thermal therapy.

18 Claims, 7 Drawing Sheets

DEVICE FOR THE APPLICATION OF ELECTRICAL STIMULATION IN COMBINATION WITH MANUAL THERAPY

PRIORITY

This application claims priority to U.S. Provisional Application No. 62/520,704 file Jun. 16, 2017.

BACKGROUND OF INVENTION

It is the objective of the present invention to provide an apparatus and the methods of using that apparatus for the application of electrical stimulation in combination with manual therapy. More particularly, the present invention includes a handheld apparatus for manual manipulation which is able to provide electrical stimulation and an applicator tip which can be cooled or heated for thermal stimulation.

The treatment of myofascial trigger points and other muscle injuries often involve manual therapy, electrical stimulation, application of heat or cold, or other physiotherapeutic modalities. Often these modalities are used in combination to treat such injuries; however, often the treatment is quite painful for the patient. The work of Travel and Simons in their text "Myofascial Pain and Dysfunction—The Trigger Point Manual" (1998) establishes the basis of the "Trigger Point" or painful locus within a muscle that can either radiate pain, or is non-radiative when depressed. As the treatment of such injuries usually necessitates the use of pressure on these areas, resolving the underlying painful area is frequently itself painful.

Similarly, the acute treatment of myofascial tears and other such musculoskeletal injuries typically involves the application of manual therapy, electrical stimulation, therapeutic ultrasound, or cold/heat application. The goal is to improve healing, reduce inflammation and decrease pain. The combination of such modalities is often more effective than using any one modality by itself, and often the application of any of these therapies can be themselves painful to the patient, as well as placing undue and repetitive stress on the hands of the therapist.

The use of certain waveforms of electrical stimulation are known to interfere with pain signal transduction, thus preventing or ameliorating the discomfort associated with the treatment of musculoskeletal/myofascial disorders, and allowing the treatment to be potentially shorter in duration and more effective overall. Additionally, the use of heat and/or cold at the same time as manual therapy/massage has other advantages that are physiologically well understood, and are the justification for the use of ice massage and other such treatments. In addition, the combination of modalities contributing to the faster recovery from musculoskeletal injuries/myofascial pain disorders results in a more cost-effective way to treat these common problems.

The prior art discloses thermo-electro stimulation probe devices (such as U.S. Pat. No. 9,084,665) capable of applying heating, cooling and/or applying electrical current and/or stimulation to a patient. The limitation of this teaching is that it does not provide a way of providing the thermo-electric stimulation along with deep muscle therapy/massage. This is because of the configuration of the probe body (see item 20 of U.S. Pat. No. 9,084,665). This probe body design does not permit deep muscle penetration in combination with thermo-electrical stimulation.

The present invention differs from the prior art in that it discloses a traditional hand held manual therapy device (often used by chiropractors, physical therapists and veterinarians) configured to be connected to an electro-stimulation device with replaceable applicator tip probes. In this arrangement, deep muscle penetration can be combined with electro stimulation. Further, the replaceable applicator tip probes can be cooled or heated for thermal stimulation.

BRIEF SUMMARY OF INVENTION

The present invention includes a hand-held apparatus for manual manipulation which is able to provide electrical stimulation and an applicator tip which can be cooled or heated for thermal stimulation. The present invention provides electrical stimulation through the use of multiple possible waveforms, in combination with manual therapy/massage and/or cold/heat application, all at the same time.

The present invention combines an ergonomic applicator for manual therapy which is conductive, but which insulates the grip held by the therapist, so that electrical stimulation can be applied through the device to the area being treated. The device allows for multiple interchangeable applicators, some of which can be chilled or heated, and exchanged during a therapy session to maintain either cold or heat on the treated area or to provide contrast therapy by alternating heat and cold application, in addition to the manual therapy and electrical stimulation simultaneously.

DETAILED DESCRIPTION OF INVENTION

The present invention will now be described in terms of the presently preferred embodiment thereof as illustrated in the drawings. Those of ordinary skill in the art will recognize that many obvious modifications may be made thereto without departing from the spirit or scope of the present invention.

The present invention is directed to address the short comings in transcutaneous electrical stimulation ("TES") devices. Specifically, these devices do not work with or come equipped with hand-held manual therapy devices. As such, typical TES devices are limited in that they can only provide electrical current to stimulate nerves or muscles. A TES device does not typically provide electrical stimulation coupled with the deep penetration of a hand-held manual therapy device as disclosed in the present invention.

Figure 2:
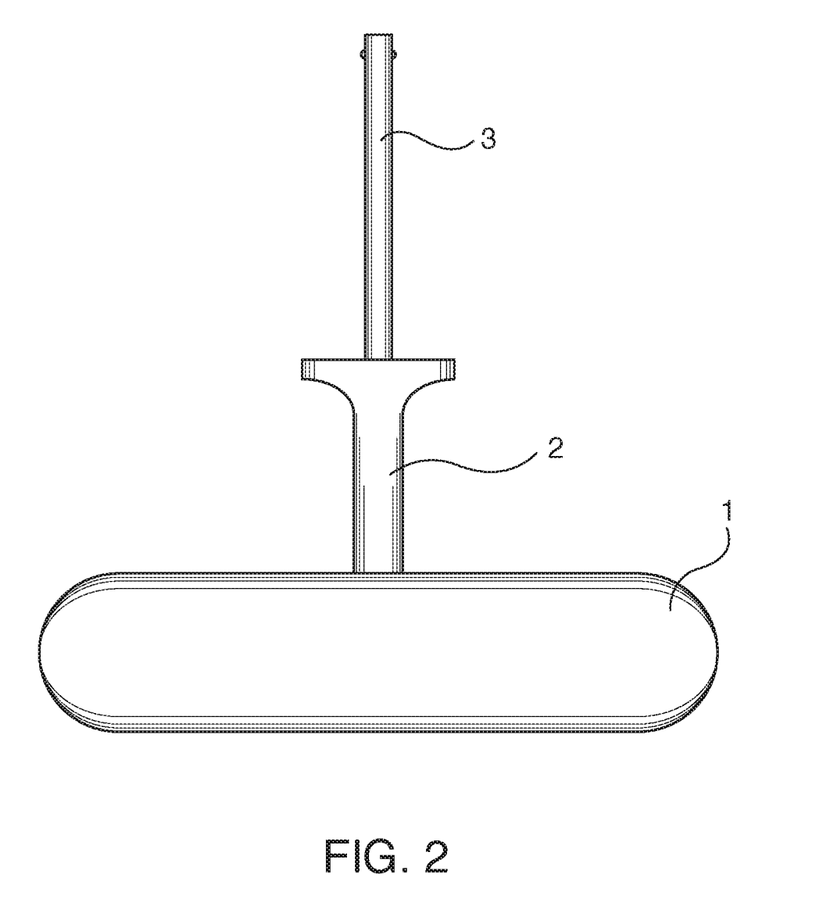
FIG. 2 is a front view of a preferred embodiment of the present invention.

In a preferred embodiment of the present invention, a hand-held apparatus is made up of a handle (1), a finger grip (2), and a shaft (3). See, FIG. 2. The handle may be of any shape and size that facilitates its function as a hand-held manual therapy device. In the preferred embodiment of the present invention, the handle is composed of a non-electrically-conductive material.

Figure 1:
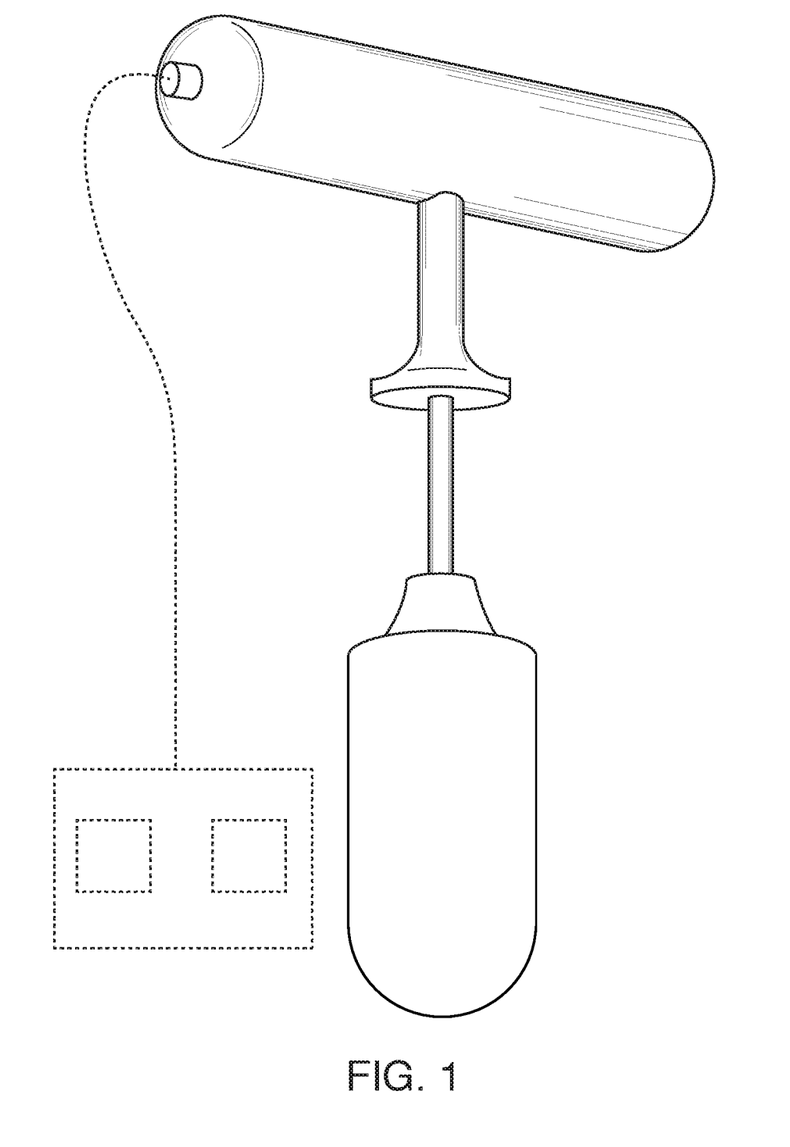
FIG. 1 is an isometric view of a preferred embodiment of the present invention.
Figure 3:
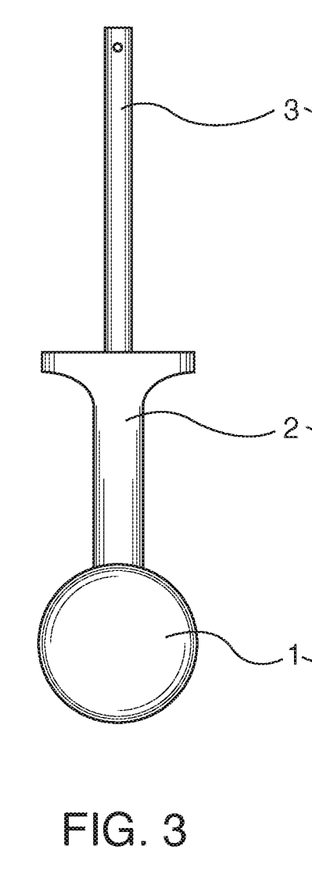
FIG. 3 is a side view of a preferred embodiment of the present invention.
Figure 4:
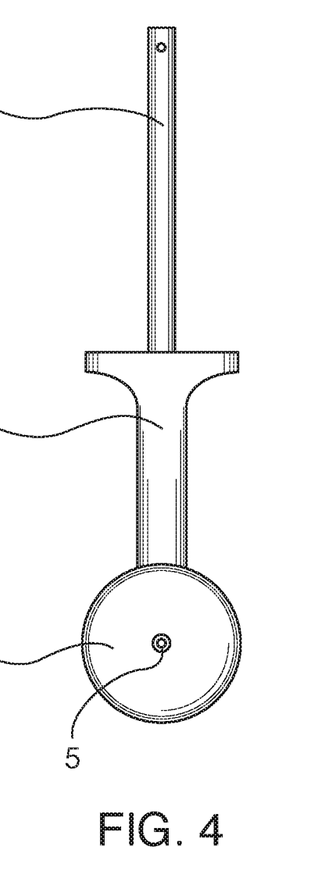
FIG. 4 is a side view of a preferred embodiment of the present invention.
Figure 5:
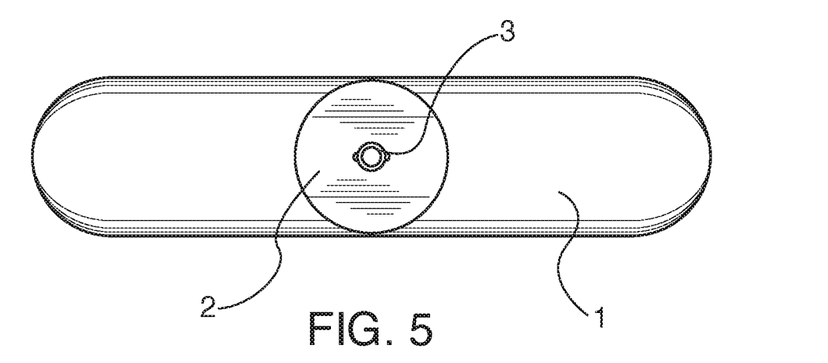
FIG. 5 is a bottom view of a preferred embodiment of the present invention.
Figure 6:
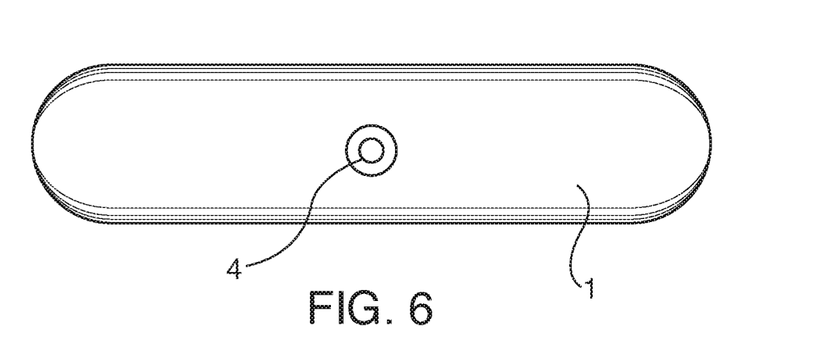
FIG. 6 is a top view of a preferred embodiment of the present invention.
Figures 7, 8:
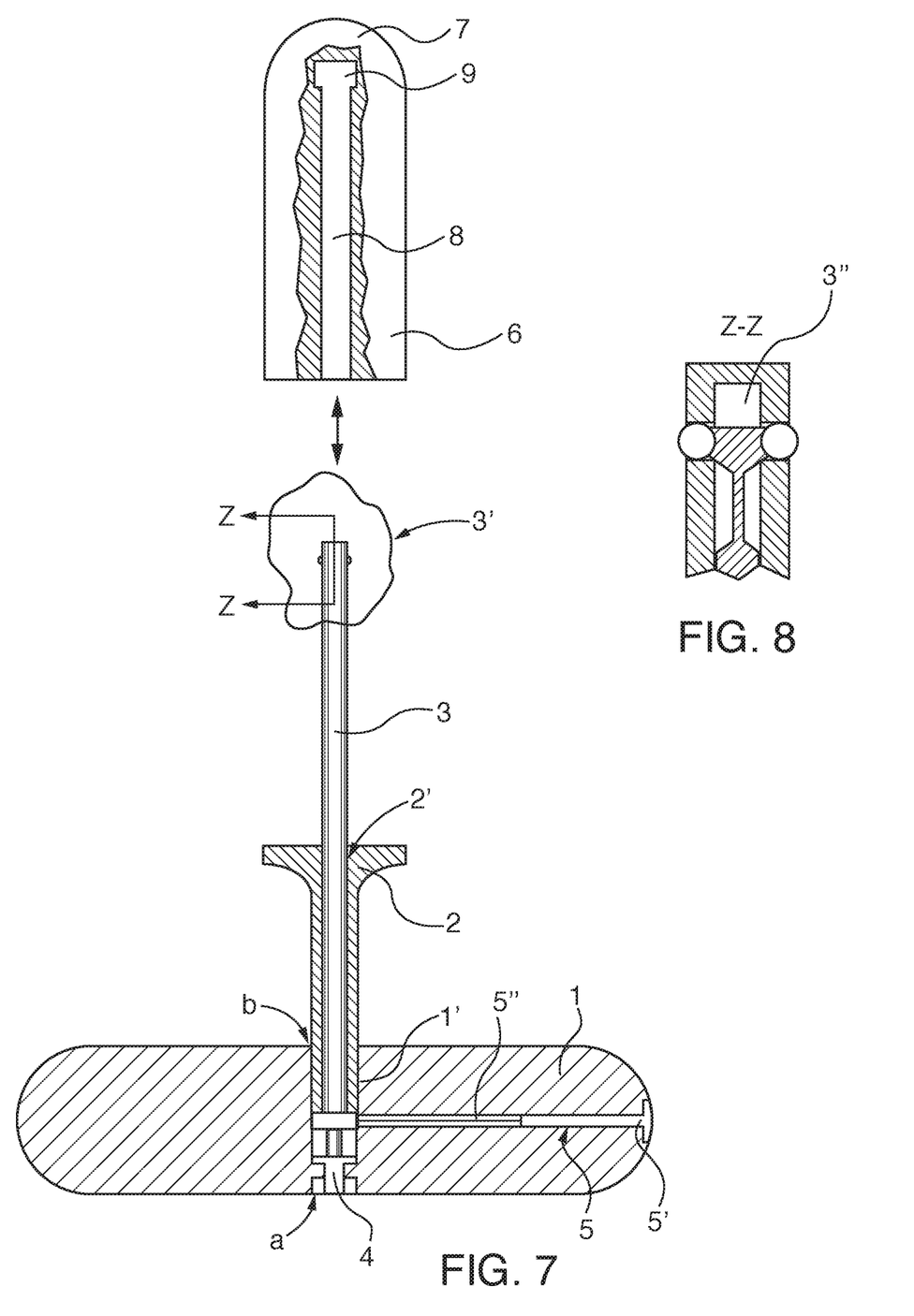
FIG. 7 is a partial cross-section front view of a preferred embodiment of the present invention.
FIG. 8 is a local cross section of the tip portion of a preferred embodiment of the present invention.
Figure 9:
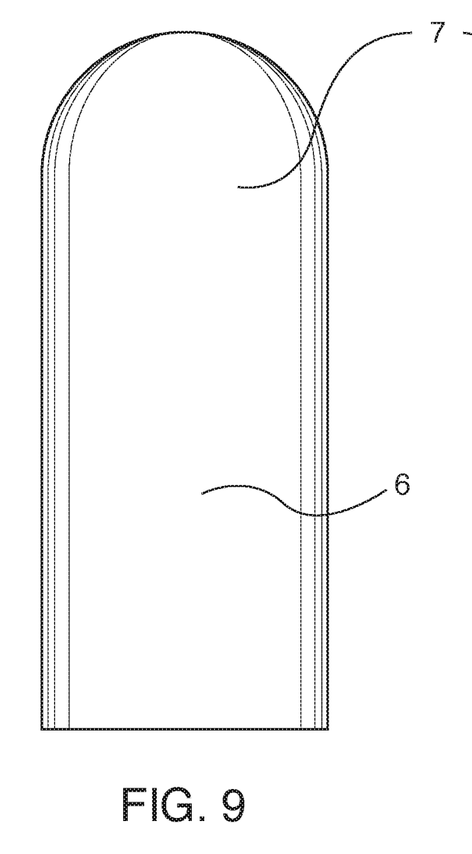
FIG. 9 is a side view of a removable applicator of a preferred embodiment of the present invention.
Figure 10:
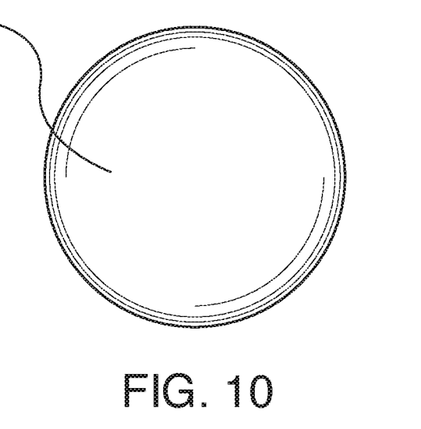
FIG. 10 is a top view of a removable applicator of a preferred embodiment of the present invention.
Figure 11:
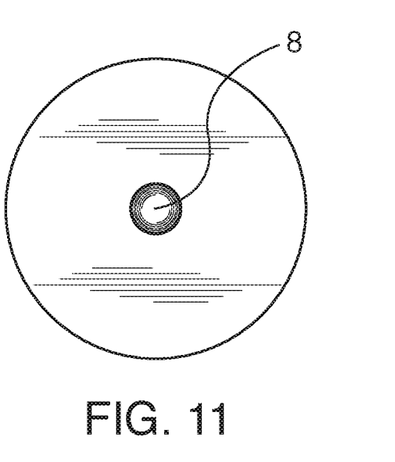
FIG. 11 is a bottom view of a removable applicator of a preferred embodiment of the present invention.
Figure 12:
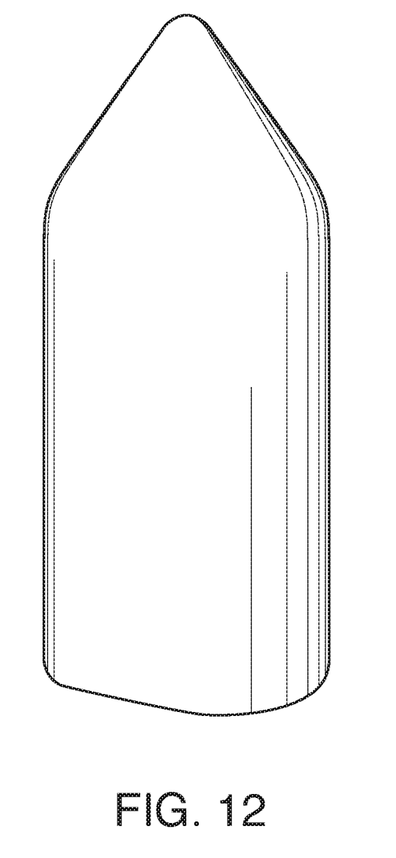
FIG. 12 is an isometric view of a removable applicator of a preferred embodiment of the present invention.
Figure 13:
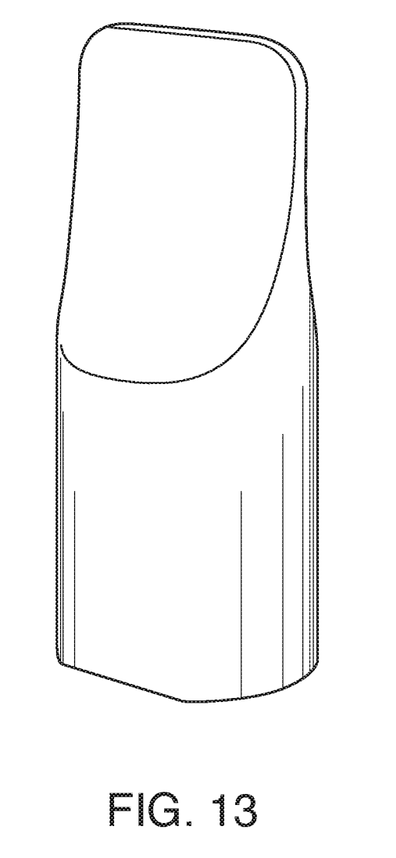
FIG. 13 is an isometric view of a removable applicator of a preferred embodiment of the present invention.

The handle (1) is cylindrical in shape and has a finger grip (2) attached, perpendicular to the long axis of the handle (1). See, FIG. 1. The finger grip (2) has an internal cylindrical thru hole (2'). See, FIG. 7. A shaft (3) with its center co-centric to the internal cylindrical thru hole (2') protrudes from the finger grip (2). FIG. 3 and FIG. 7. The handle (1) has a stepped through hole (1') at the center of the long axis of the handle (1) resulting in two holes—one at the top of the handle (a) and one at the bottom of the handle (b). See, FIG. 7. The hole at the top of the handle (a) receives a button (4) which connects to shaft (3) and allows for the release of a spring located inside the shaft (3) connected to two balls which protrude and retract from shaft 3 at its end (3") to allow for the secure placement onto the shaft (3) of various types of applicators (6). See, FIG. 7, FIGS. 9-13. The hole at the bottom of the handle (b) receives the finger grip (2) with the shaft (3) inserted into the internal cylindrical thru hole (2') of the finger grip (2). See, FIG. 7.

Further, the Handle (1) has a hole (5) along its long axis that terminates and breaks through at the stepped thru hole (1') at the center of the long axis of the handle (1). See FIG. 7. This hole (5) allows for insertion of a female electrical jack (5') and wire (5") into the handle (1) and connection with the shaft (3). The female electrical jack (5') is designed to accept the male electrical jack from any commercially available TES unit. The wire (5") connects the female electrical jack (5') to the shaft (3). In this way, a commercial available TES unit can simply be plugged into the handle (1) of the device (FIG. 1) of the instant invention allowing electrical waves to be transmitted down the shaft (3) through an applicator tip (6) removably attached to the shaft (3) and secured by the spring loaded retention device (FIG. 8) in the tip of shaft (3). See, FIG. 1, FIG. 7 and FIG. 8. The shaft (3) is composed of electrically-conductive material. The shaft (3) receives and conducts the electrical current through the wiring and the electrical jack.

The tip of the shaft (3') has a quick release device (3") that is comprised of two spring loaded balls that protrude from opposing sides of the shaft (3) at (3') to secure and release the various applicators (6) to the end of the device. See, FIG. 7 and FIG. 8. The quick release device is operated through the button (4) in the handle (1). See, FIG. 7. When the button (4) is pushed, the tension in the spring locate in shaft 3 is released and the protruding balls in shaft are free to recess back into the shaft when an applicator (6) is pushed onto or removed from shaft (3). See, FIG. 7 and FIG. 8. Conversely, when the button (4) is released, the spring located in shaft (3) is permitted to expand and the protruding balls in shaft (3) are locked into place once the applicator (6) is secured on shaft (3). See, FIG. 7 and FIG. 8. The quick release mechanism may be a spring or cam system or any other similar system.

In a preferred embodiment of the present invention, the applicator (6) is most often made of stainless steel or other electrically conductive material and should be made of durable and nonporous material. See, FIGS. 9-13. Further, the applicator (6) material should be thermally conductive and temperature adaptive and resistant so that it can be heated or cooled to different temperatures and can withstand the temperature changes without being damaged.

The applicator (6) has an applicator tip (7) which is the portion of the applicator applied to the patient's body when the device of the present invention is used. See, FIG. 1. and FIGS. 9-10. The applicator (6) has an internal bore (8) which is received onto shaft (3). See, FIG. 7 and FIG. 11. The applicator (6) is locked onto shaft (3) by the quick release mechanism (3") expanding into notch (9) in applicator (6). See, FIG. 7. The applicator (6) is removed from shaft (3) by depressing button (4) and contracting the quick release mechanism (3") from notch (9) in applicator (6). See, FIG. 7.

In a preferred embodiment of the method of the present invention, an applicator (6) with a particular tip (7) selected by the therapist for the patient in question will be heated or cooled as required. Thereafter, the applicator (6) will be secured onto the device, a commercially available TES unit will be electrically connected to the device (1) by plug-in female electrical connection (5'). The TES unit will be activated and the appropriate wave setting set by the therapist. The therapist will then apply manual therapy to the patient by means of the device with the applicator (6) installed and thermally treated and transmitting the waves generated by the TES though the handle (1), down the shaft (3) and through the applicator (6).

Many applicator tip shapes and sizes can be adapted for use with the present invention without departing from the spirit or scope of the invention as set forth herein. See, FIGS. 9, 12 and 13. Specifically, the removable applicator tip may be shaped like an inverted cone with a hemispherical tip portion; have a flattened end; come to a point; have a generally rounded end; have a mushroomed rounded end; or have a mushroomed rounded end with a molded wave pattern.

Those of ordinary skill in the art will recognize that the embodiments just described merely illustrate the principals of the present invention. Many obvious modifications may be made thereto without departing from the spirit or scope of the invention as set forth in the appended claims.

The invention claimed is:

1. A hand held manual physical therapy device comprising:
   a. a handle with a shaft and an electrical connection jack;
   b. the shaft protrudes from the handle and has a distal end;
   c. removable applicator tip probes comprised of electrically and thermally conductive material removeably attachable to and detachable from the distal end of the shaft, said applicator tip probes are electrically connected to the electrical connection jack in the handle; and wherein the handle is cylindrical with a finger grip protruding perpendicular from the center of the cylindrical handle and wherein the shaft protrudes from the finger grip.

2. The device of claim 1, wherein the removable applicator tip probe comprises a plurality of external surfaces and is configured to articulate against an individual's skin and the underlying muscle when the device is operated by manually moving the device across the individual's skin such that the removable applicator tip probe provides the skin and underlying muscle with a combination of electro-stimulation and physical force.

3. The device of claim 1, wherein an electro-stimulation unit is attached to the handle by means of the electrical connection jack.

4. The device of claim 3, wherein the removable applicator tip probe comprises a plurality of external surfaces and is configured to articulate against an individual's skin and the underlying muscle when the device is operated by manually moving the device across the individual's skin such that the removable applicator tip probe provides the skin and underlying muscle with a combination of electro-stimulation and physical force.

5. The device of claim 3, wherein a plurality of removable applicator tip probes are selectively attachable to and detachable from the distal end of the shaft.

6. The device of claim 3, wherein the removable applicator tip probe is cylindrical with a hemispherical tip portion.

7. The device of claim 3, wherein the removable applicator tip probe is an inverted cone with a hemispherical tip portion.

8. The device of claim 3, wherein the removable applicator tip probe has a flattened end.

9. The device of claim 3, wherein the removable applicator tip probe comes to a point.

10. The device of claim 3, wherein the removable applicator tip probe has a rounded end.

11. The device of claim 3, wherein the removable applicator tip probe has an expanded mushroomed rounded end.

12. The device of claim 3, wherein the removable applicator tip probe has an expanded mushroomed rounded end with a molded wave pattern end.

13. The device of claim 1, further comprising a quick release device disposed on the distal end of the shaft.

14. The device of claim 13, further comprising a button disposed on the handle, wherein the button is configured and disposed to operate the quick release device.

15. A method for using the hand held manual physical therapy device, the method comprising:
   obtaining a hand held manual physical therapy device, comprising a handle with a shaft and an electrical connection jack;
   the shaft protrudes from the handle and has a distal end;
   removable applicator tip probes comprised of electrically and thermally conductive material removeably attachable to and detachable from the distal end of the shaft, said applicator tip probes are electrically connected to the electrical connection jack in the handle;
   connecting the device to an electro-stimulation unit by means of the electrical connection jack in the handle of the device and wherein the handle is cylindrical with a finger grip protruding perpendicular from the center of the cylindrical handle and wherein the shaft protrudes from the finger grip;
   inserting a tip probe onto the shaft of the device;
   manually moving the hand held manual physical therapy device across an individual's skin such that the tip probe provides the skin and underlying muscle with a combination of electro-stimulation and physical force.

16. A method for using the hand held manual physical therapy device, the method comprising:
   obtaining a hand held manual physical therapy device, comprising a handle with a shaft and an electrical connection jack;
   the shaft protrudes from the handle and has a distal end;
   removable applicator tip probes comprised of electrically and thermally conductive material removeably attachable to and detachable from the distal end of the shaft, said applicator tip probes are electrically connected to the electrical connection jack in the handle; and
   connecting the device to an electro-stimulation unit by means of the electrical connection jack in the handle of the device and wherein the handle is cylindrical with a finger grip protruding perpendicular from the center of the cylindrical handle and wherein the shaft protrudes from the finger grip;
   heating or cooling a tip probe;
   inserting the heated or cooled tip probe onto the shaft of the device;
   manually moving the hand held manual physical therapy device across an individual's skin such that the tip probe provides the skin and underlying muscle with a combination of electro-stimulation, thermo-stimulation and physical force.

17. The method of claim 15, wherein the tip probe is cylindrical with a hemispherical tip portion.

18. The method of claim 16, wherein the tip probe is cylindrical with a hemispherical tip portion.

\* \* \* \* \*